United States Patent [19]

Parmelee et al.

[11] Patent Number: 4,504,267
[45] Date of Patent: Mar. 12, 1985

[54] APPARATUS FOR INTRAVENOUS INJECTION OF LIQUIDS

[76] Inventors: William H. Parmelee, 5036 W. Library Rd., Bethel Park, Pa. 15102; Roger D. Sutton, 360 Avon Dr., Pittsburgh, Pa. 15228

[21] Appl. No.: 211,256

[22] Filed: Nov. 28, 1980

[51] Int. Cl.³ ............................................. A61M 5/00
[52] U.S. Cl. ..................................... 604/134; 604/174
[58] Field of Search ................... 128/214 R, DIG. 12, 128/214 F; 604/134, 131, 174, 182, 181

[56] References Cited

U.S. PATENT DOCUMENTS

| | | | |
|---|---|---|---|
| 2,915,222 | 12/1959 | Purinton | 604/182 X |
| 3,468,308 | 9/1969 | Bierman | 128/DIG. 12 |
| 3,547,322 | 12/1970 | Dawson | 128/214 R |
| 3,565,292 | 2/1971 | Jinotti | 128/DIG. 12 |
| 3,595,232 | 7/1971 | Liebinsohn | 604/134 |
| 3,734,351 | 5/1973 | Gaudin | 128/214 F |
| 3,895,741 | 7/1975 | Nugent | 128/214 F |
| 3,952,989 | 4/1976 | Hatcher | 248/453 |
| 4,087,864 | 5/1978 | La Bove et al. | 128/214 R |
| 4,337,769 | 7/1982 | Olson | 604/131 |

FOREIGN PATENT DOCUMENTS 2042091 9/1980 United Kingdom ....... 128/DIG. 12

*Primary Examiner*—Marion McCamish
*Assistant Examiner*—Nancy A. B. Swisher

[57] ABSTRACT

To replace the usual gravity apparatus for intravenous injection of fluid in the body, there is provided a portable casing into which the usual collapsible liquid-containing flask is placed between two separate panels, one or both of which are movable toward and away from the other. The separation of the plates is against the force of prestressed torsion springs and these springs force the plates together toward a closed position when they are released after the flask has been placed between them to apply pressure to the flask and expel the liquid from the flash through a flexible tube having a discharge terminal. An actuating extension attached to the movable plate or plates is arranged to releasably hold them in separated positions when a flash is being removed or inserted between them. A garment is provided in which this apparatus may be retained when the patient is ambulatory.

18 Claims, 13 Drawing Figures

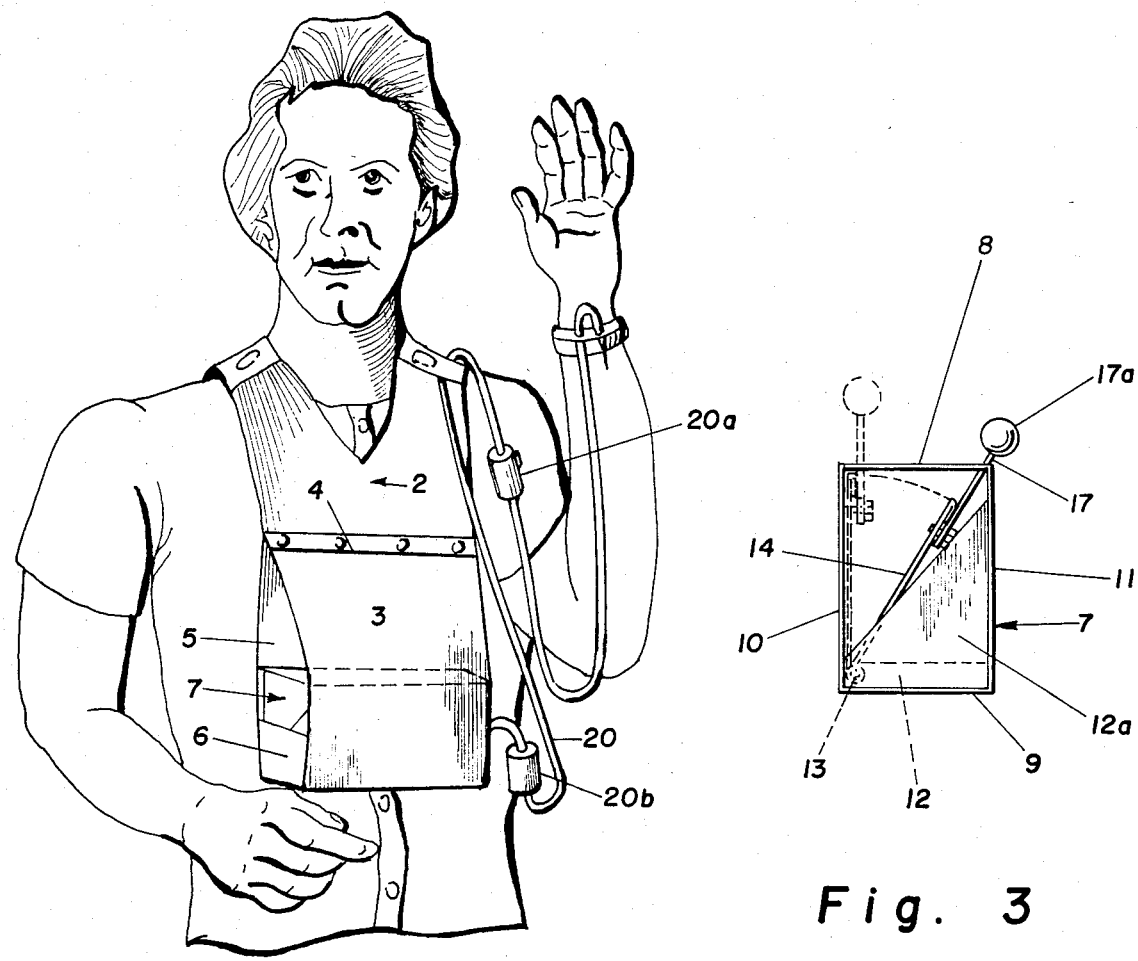
Fig. 1
Fig. 3
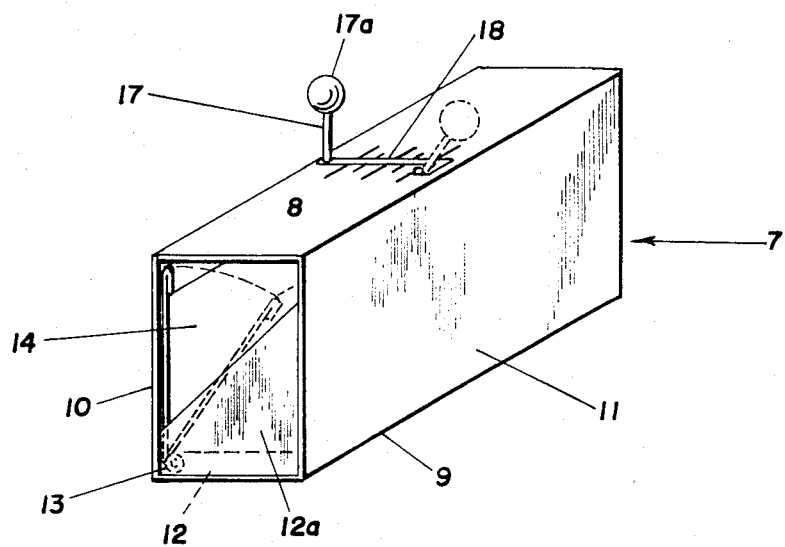
Fig. 2

APPARATUS FOR INTRAVENOUS INJECTION OF LIQUIDS

BACKGROUND OF THE INVENTION

This invention is for apparatus for the sustained injection of liquid intravenously, as distinguished from a quick shot from a hypodermic needle, and is for an apparatus for this purpose that is less cumbersome and more convenient than the gravity method presently in use where a plastic flask, formerly a bottle, is suspended from an elevated hook at a level well above the patient and the liquid flows by gravity from the flask through a long flexible plastic tube, on the free end of which is a discharge terminal either in the nature of a needle or catheter entered into a patient's vein, usually but not necessarily in the forearm.

The most common means for suspending the flask comprises a metal pole on a base provided with casters to enable it to be rolled about the room and hallway and which generally has one or more radially extending arms at the top. Each arm has a hook at the end from one of which a plastic flask containing the liquid to be injected is hung.

This post arrangement is quite heavy, the base being weighted so that the post will not easily tip over. If the patient has to be moved, this pole must go along with him; it must be maneuvered around when the room is being cleaned or when the patient is being transferred from a bed to a chair or another bed.

Many patients could desirably be mobile and free to ambulate through the corridor or to a lounge or to travel back and forth to the bathroom except for the limitation against freedom of movement imposed by the need to pull, or have an attendant pull, the pole and suspended flask whenever he moves. Trips in the elevator to X-ray or other diagnostic equipment are likewise often hampered by this need to keep the pole and suspended flask close to the patient. There is the ever present risk of the long hose between the flask and the patient becoming caught or hung up on a doorknob or other protruding object, sometimes resulting in a painful flesh wound where the discharge terminal is pulled from the patient's vein.

Various attempts have heretofore been made to dispense with the gravity method of injecting the liquid, but so far as we are aware, they have required specially shaped bags of cumbersome shape and have been quite unacceptable.

BRIEF DESCRIPTION OF THE PRESENT INVENTION

As generally manufactured, the fluid filled plastic bags containing the liquid to be intravenously administered are, when filled, oblate in transverse section with the length from end to end exceeding the maximum diameter. They have a tab at one end provided for their suspension in the manner hereinbefore described. At the other end there is an outlet fitment to which the flexible discharge tube is attached.

In general the present invention comprises first an elongate, rigid or nondeformable enclosure having two generally coextensive planar panels, at least one of which is movable toward and away from the other and which, when their confronting faces are separated, provide between them a cavity into which a liquid filled flask, as described and now in general use, may be placed. Only the tab at one end of the flask and the discharge fitment at the other end of the flask protrude from between the panels, or if they do not protrude, are accessible from the ends of the cavity. The panels, or at least the movable one if but one is movable, is spring-biased so that when the flask is confined between them, the flexible plastic flask will be squeezed to expel the liquid therefrom through the discharge tube and discharge terminal into the body of the patient.

While, as previously stated, the idea of replacing gravity in a device for this purpose is not broadly new, including the use of tension or compression springs, the movable panel or panels of the present invention are urged, one toward the other, by torsion springs which are already under pressure when assembled into the enclosure with the plates together in close face-to-face relation and which are additionally tensed when the plates are separated to receive the liquid-filled flask between them. Moreover, the apparatus is so constructed that the arc of rotation through which the springs are tensed for receiving the flask and, thereafter, in the reverse direction "unwind", is desirably less than 40° and preferably of the order of about 30°. Limited in this way, the drop in spring force or pressure gradient is but a small percentage of the total available spring tension and, for practical purposes, is negligible between the start and finish of dispensing the contents of a standard one-liter flask.

In the present preferred embodiment of the invention there is a rigid casing which when in use has all exterior walls immovably fixed with relation to one another, the length of said casing exceeds in transverse section the width from top to bottom and the transverse distance from side to side. The ends of the casing are partly open and partly closed. One side panel of the casing comprises a fixed pressure surface or panel. Within the casing is a movable pressure plate that confronts said fixed pressure panel. It is hinged within the casing along its bottom edge with hinge means comprising a plurality of coiled torsion springs prestressed to forcefully urge the pressure plate against the fixed pressure panel. An operating lever fixed to this panel and projecting through a transverse slot in the top of the casing enables the pressure plate to be pulled back on its hinge against the pressure of the torsion springs through an arc of between about 30° and 40° to further stress the torsion springs and to enable the plastic bag of a shape and size now generally in use, filled with the liquid to be administered to the patient, to be inserted lengthwise of the casing into the somewhat V-shaped cavity between the fixed panel and the pressure plate.

Upon release of the operating lever the pressure plate will squeeze the liquid filled plastic bag transversely of its length to expel the contents from the bag through the usual small diameter tube with its usual pinch-type flow control valve into the vein of the patient, the air from the tube being first expelled before the injection needle or catheter is inserted into the vein.

Our invention includes an easily applied garment, somewhat resembling a carpenter's apron or halter, but instead of having an assortment of pockets, it provides a single pocket, at the general level below the shoulders and above the level of the wearer's thighs, which is closed across the top and open at each end, much like a cold-weather hand muff. This open-ended pocket is of a size to loosely receive the foregoing elongate, generally rectangular apparatus just described and suspend it from the patient's shoulders but above the level of the patient's thighs where it will not interfere with walking or sitting, but with the flask visible from the ends of the pocket so as to readily enable the tube connection on the flask to be directed toward the right or left side of the patient. Gussets at each end of the pocket may be provided to prevent the dispensing box or apparatus from sliding out of the pocket, but the lever at the top of the casing will not be accessible to the patient to invite tampering.

With the weight of the enclosure or "box" and the flask contained in it suspended from the patient's shoulders, the patient can ambulate and stand or sit freely, and if he gets into his bed, the garment with the casing therein, or the casing alone, may be placed on a bedside table.

BRIEF DESCRIPTION OF THE DRAWINGS

Our invention may be more fully understood by reference to the accompanying drawings in which:

FIG. 1 is an illustrative view disclosing how the casing and garment are combined in use and carried by the patient who is then free to move about;

FIG. 2 is a small scale perspective view showing the general shape of the box or dispenser with the pressure plate operating lever in the cocked or rear limit of its travel and ready to receive the full flask of liquid;

FIG. 3 is an end view on a larger scale than FIG. 2 and with the movable plate in the extended non-operating position for shipment or storage;

Figure 4:
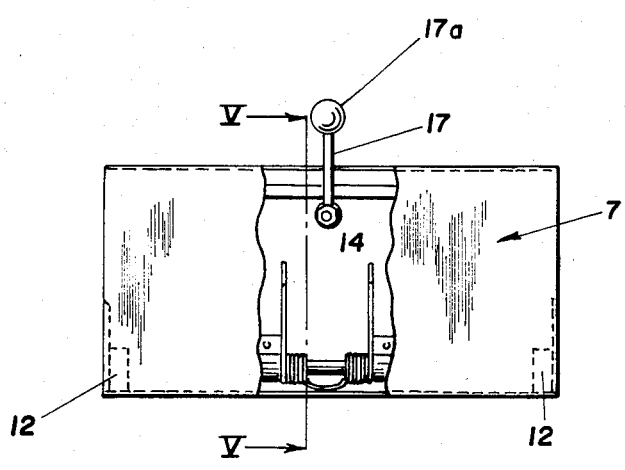
FIG. 4 is a side elevation on the same scale as FIG. 3 but with part of the rear or long side panel of the box broken away to show the hinge and torsion spring assemblies for urging the pressure plate forcefully toward the front panel of the casing and which comprises the cooperating fixed pressure plate.

Referring first to FIG. 1, which is illustrative of the entire combination as applied to an ambulatory patient, there is first a garment 2 in the general form of a carpenter's apron or halter that has a strap over each shoulder and which straps come together and button at the back, or which otherwise provides an opening for the patient's head and neck. The fabric comprising the front panel 3 of the garment is folded and stitched or buttoned, as indicated at 4, to form a horizontal loop or open-ended tubular pocket 5. Across each lower open end of the pocket there is a gusset or strap 6.

The liquid injection unit indicated generally as 7 is received in this muff-like open-ended pocket or pouch and the straps or gussets 6 prevent the unit from sliding unintentionally out of the pocket once it has been put into place, with the pocket being open at both ends whereby the discharge tube of the flask can be optionally positioned toward the patient's right or left arm. However, the dimension of the pocket is such that the unit or casing can be raised above the gussets 6 for removal and likewise permit its ready insertion into the pocket.

Leaving the description of the garment and its use for further explanation, the unit 7 comprises a horizontally elongate casing of fixed overall rectangular section, both crosswise and lengthwise, with the height of the section being less than its length but greater than its width or thickness. The top of the box is indicated by the number 8, the bottom is 9. Side panel 10 may be referred to as the front or pressure panel, and the opposite one 11 is the rear panel.

Figure 6:
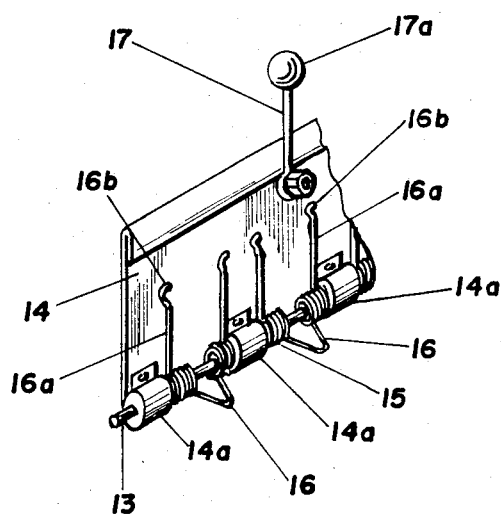
FIG. 6 is a fragmentary perspective view of a portion of the pressure plate, its bearing on the pintle shaft and the double torsion spring units.

Set in each open end of the box or casing at the bottom is a crossbar or bearing block 12 and extending lengthwise of the casing in the corner area between the front wall and the bottom of the box there is a stiff shaft or pintle 13. There is a movable pressure plate 14 inside the fixed exterior walls of the casing which is only slightly shorter in length and slightly less in height than the front side panel 10, which it confronts. The lower edge of the movable pressure plate 14 is formed with a plurality of spaced extensions that are rounded into sleeve bearings 14a through which the shaft 13 passes so that the plate 14 hinges or is free to swing in an arc of between about 30° or 40° from a position parallel with the front panel of the box to form between the front panel and the pressure plate a somewhat V-shape cavity long enough to receive a standard one-liter bag when it is full but with ends, particularly the outlet end, protruding for access at one end of the casing (FIG. 6). It may be used, of course, with smaller bags and for bags of other shapes made especially for use in a generally similar unit.

There is a double torsion spring 15 on the pintle shaft 13 between each two bearing sleeves 14a. The torsion spring 15 preferably comprises two coaxial coils with a closed connection loop 16 between the two coils, this loop constituting a rotation stop contacting the interior of the bottom of the box to prevent the springs from rotating in a counterclockwise direction when viewed, as shown in the drawings, with the front or pressure panel of the casing at the left. There is an important advantage in reducing weight by having one wall of the box as a pressure plate.

The free ends of each of the coil springs have an integral extension 16a with a terminal offset 16b. In the assembly the coil springs are tensed through an arc of about 90° or more when the pintle shaft 13 is in place, with the extensions fixed against the back surface of the pressure plate and with the pressure plate parallel with and close to the front panel with only sufficient space between to accommodate the empty flask after the liquid has been drained from it. Generally, the mechanics of the spring and plate assembly is comparable, in effect, to a familiar screen door hinge but with the hinge pin horizontal instead of vertical, the pressure plate corresponding to the door, the two spring extensions to one leaf of the door hinge, the loop 16 to the other leaf of the spring hinge and the bottom of the case to the door frame.

There are triangular partial end walls 12a at each end of the casing which cover the triangular open space behind the plate 14 to exclude persons from putting objects in the casing or having access to the springs and which, along with blocks 12, prevent the pressure against the front panel from distorting the box into a parallelogram. This enables the casing to be made of lighter gauge metal than if they were not provided.

Figure 7:
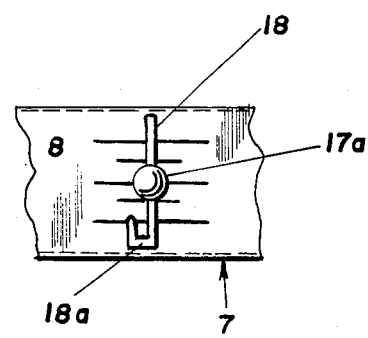
FIG. 7 is a fragmentary top plane view of the casing showing the transverse slot with a "bayonet" type offset at the rear end, the movable plate operating lever being shown in transverse section, below its terminal knob, and with distance graduations along the edges of the slot to indicate by travel of the lever the extent of depletion of the contents of the flask.

With our invention there is a stiff rod or lever 17 welded or otherwise fixed to the pressure plate 14 with the rod extending upwardly through a transverse slot 18 in the top of the box. At the free upper end of the lever there is a knob 17a. The rear end of the slot 18 has a bayonet type offset notch 18a (see FIG. 7).

In use, the lever may be pulled from its forward position where the front panel of the box and the pressure plate are substantially parallel rearwardly along the slot and at the rear end flexed sideways into the bayonet notch 18a. In pulling the lever and rocking the pressure plate rearwardly, the already biased torsion springs will be further wound or stressed through an additional arc of perhaps 30° but desirably not exceeding 40°, thereby increasing the spring pressure substantially because of their already stressed condition The spring tension tending to pull the pressure plate forward firmly holds the lever 16 in the bayonet notch 17a against accidental release.

With the lever thus retracted, and "cocked", the box is up-ended and the plastic flask, filled with liquid to be injected, is lowered into the cavity between the front panel of the box and the retracted pressure plate. With the flask inserted, with its tube or outlet fitment at that side of the patient's body, right or left, where it is proposed to insert the needle or catheter, the nurse attaches the conventional tube 20 (FIG. 1) with a needle or flexible intravenous catheter at its discharge end and the usual roller type of squeeze valve or other flow control means 20a now commonly used in intravenous injection apparatus, between the bag and the discharge end of the tube. If there is a sight glass type of drop feeder in the tube and which is usually close to the flask, the tube and sight glass should loop downward from the outlet end of the glass as indicated at 20b in dotted lines in FIG. 1. Usually the patient is and should be lying down when injection is first started and the outlet end of the sight glass will be lower than the box, so there is initially no difficulty in adjusting the drop per-minute flow with the roller-valve usually provided on the tube for this purpose. Thereafter when an empty flask must be replaced with a fresh one, the tube is disconnected from the empty flask and reconnected to the full one. Just as with gravity flow where the elevation of the needle with respect to the level of the flask varies the gravity flow, it may similarly vary with pressure flow as here provided; but such minor variations are not, in most cases where the patient is mobile, significant.

The top of the box may have graduations along one or both edges of the slot to indicate by travel of the lever the general extent to which the flask may have emptied at any particular time and the approaching need for replacement of the flask or termination of the treatment. This can also be closely estimated after little experience by looking into the end of the box and observing the position of the pressure plate.

There is a unique advantage in the use of what we term a prestressed torsion spring. In a torsion spring an end of a spring wire coil is rotated about the axis of the coil while the other end is fixed, the direction of rotation being such that if the coil were not spring wire resisting this winding action, another convolution would be added to the coil. Being spring wire, it resists this winding. If, for example, the free end is initially rotated through an arc of 90°, the spring will inherently exert force to unwind until that 90° has been relieved. In a typical screen door hinge, for example, opening the door 90° additionally stresses the hinge spring to an extent that when the door is released, it will close the door with considerable force and sufficient tension still remains to resist the opening of the door by normal wind or house pets, thus showing that with prestressing there is reserve energy to assure complete or substantially complete utilization of the contents of the flask.

With the present invention, it may be assumed that the spring is prestressed through an arc of 90° or 120° when it is installed in the casing so that even when the pressure plate is parallel with the front plate of the casing, it is exerting a substantial pressure against the pressure plate. When the lever is operated to pull the plate to its open or cocked position for the reception of a full flask of liquid, the spring is further stressed through an additional arc of between only 30° to 40° so that squeezing the full bag from its full to its empty position has exhausted only a fraction of its potential force and with a relative moderate pressure decrease comparable to the decrease in the force of gravity as a flask suspended vertically from an elevated hook decreases as the liquid level in the flask lowers. Importantly, however, with a torsion spring in contrast to a tension or compression coil spring, the dimension of the torsion spring does not noticeably undergo a change in size whereas a coiled tension or compression spring must shorten or lengthen substantially, as the case may be, for prestressing plus the added tension for the modest gradient decrease in pressure through its normal operating range. Additionally with the provision of the prestressed torsion springs continuing to exert a fixed pressure on the pressure plate, should the patient then not have attention as soon as the bag is empty, the bag and any residual liquid or air in the flask will remain under constant pressure sufficient to preclude backflow of blood from the patient's vein into the tube. Also, a plurality of torsion spring units may be arranged side by side along the length of the casing and pressure plate to act cumulatively instead of requiring a single heavy spring, and thereby reduce bending pressure on the relatively thin lightweight pressure plate. While we prefer coiled torsion springs about the pintle, but coaxial with the pintle, the pintle itself could be made to twist about its own axis and comprise a torsion bar spring.

Figure 5:
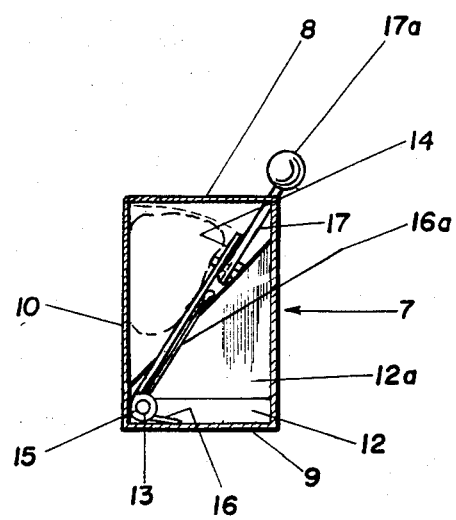
FIG. 5 is a transverse section in the plane of line V—V of FIG. 4, and showing in dotted lines the outline of a full flask of liquid in place for use.
Figure 8:
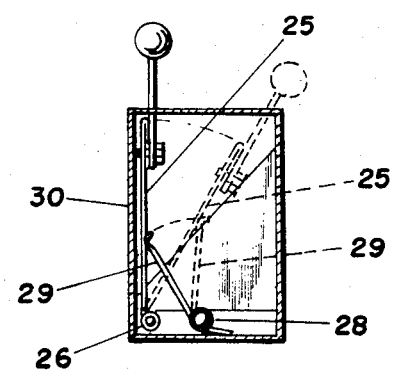
FIG. 8 is a schematic transverse section similar to FIG. 5 showing a modified arrangement in which the torsion spring assemblies on a separate shaft speced from but parallel with the hinge pintle for the pressure plate and exerting pressure through a sliding or rolling engagement with the pressure plate.

The modification schematically illustrated in FIG. 8 is essentially the same as that shown in FIG. 5 except the pressure plate 25 is on a pintle 26 as in the preceding figure, but the torsion springs 27 are on a separate shaft 28 parallel with the pintle shaft. They apply pressure to lever means 29 having a sliding or roller contact with the pressure plate, urging it forward against the front panel 30 of the casing. As in the unit first described, the torsion springs are prestressed to such extent that if the front panel of the casing were removed, the pressure plate would be pressure driven from 90° to perhaps 180° beyond the plane of the front panel before exhausting the spring pressure, or 90° to 180° beyond its normal required range of movement of the pressure plate between 30°, or even less, and 40°.

Figure 9:
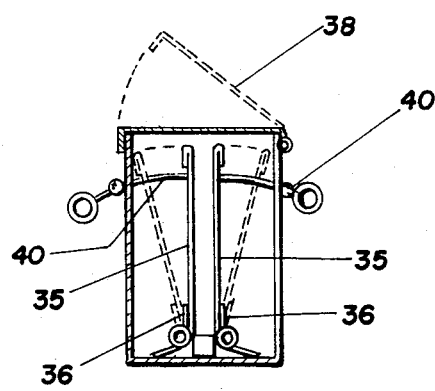
FIG. 9 is a schematic transverse section through a modified construction wherein there are two confronting pressure plates hinged along their parallel lower edges to the bottom of the casing by torsion spring hinges.
Figure 10:
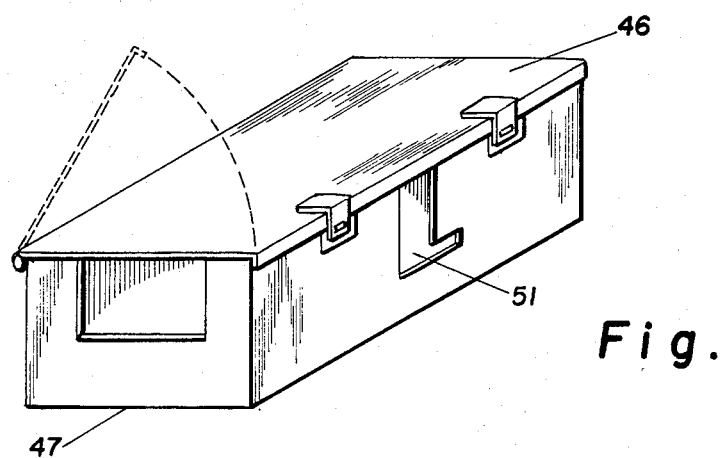
FIG. 10 is a perspective view of another modification wherein the box has a hinged cover and the pressure plate is urged by spring pressure toward the cover.

In the modification shown schematically in FIG. 9, there are two confronting pressure plates 35, each on separate prestressed spring hinges at 36 along their respective bottom edges. These may be similar to those shown in FIGS. 2 to 5 or separate hinges resembling screen door hinges. The casing 37 has a hinged top 38 so that the plates can be opened, book-like, to spread them apart to enable the flask 39 to be placed in the space between them. Both ends of the flask have openings therein affording access to the ends of the flask. In this modification knotted pull cords 40 passing through keyhole-type openings in the side panels are used as an alternate to lever 17 in the preceding figures to spread and hold the plates apart against spring pressure until the flask is inserted.

Figure 11:
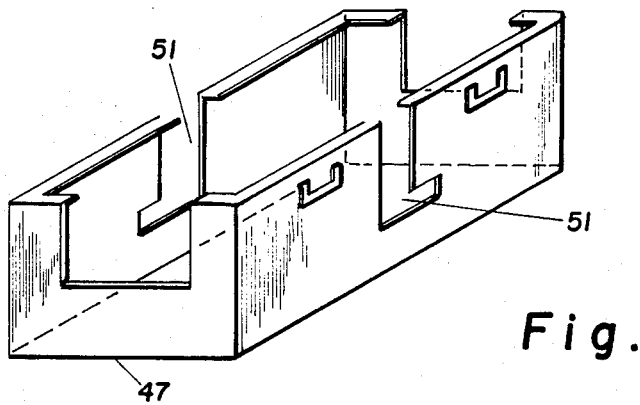
FIG. 11 shows the box of FIG. 10 without the lid.
Figure 12:
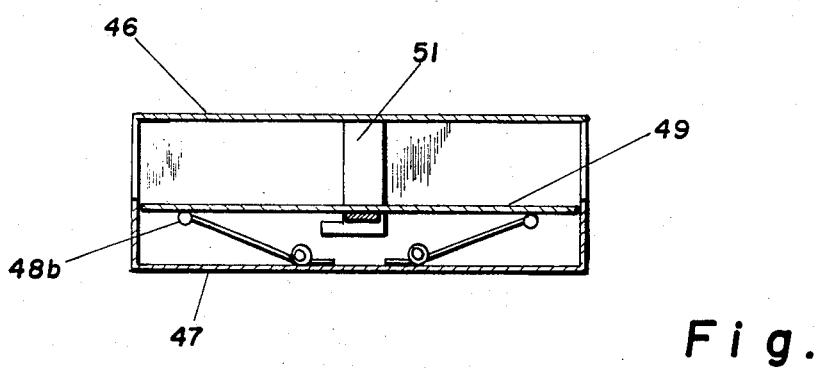
FIG. 12 is a longitudinal section through the assembly showing the interior arrangement.
Figure 13:
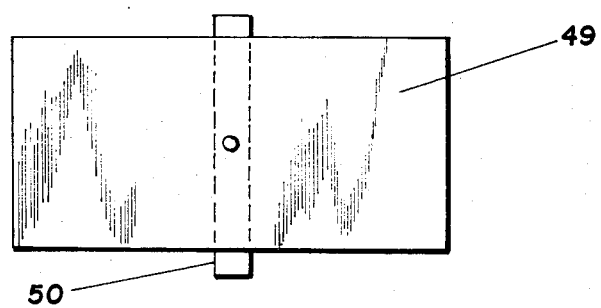
FIG. 13 is a plan view of the movable pressure plate apart from the assembly.

FIGS. 10 to 13 disclose a still further modification wherein there is a generally rectangular box 45 with a hinged cover 46, as indicated at 46a, where only the end of the hinge extending along the distal side of the box is visible. It has loop-type fasteners schematically indicated at 46b on the near edge of the lid of a familiar type, for example, such as those often seen on suitcases. As seen in FIG. 11, where, for clarity of illustration, the lid is removed, there is an opening in each end wall of the box. Also there is an in-turned narrow lip or flange 45b either partially or entirely along the top edge of each side wall and may be, as shown, also on the end walls. The bottom of the box is designated 47. As schematically indicated in the drawing, there are at least two strong torsion springs 48 such as "rat trap" type springs with extended arms 48a with a transverse connecting bar at the ends on which is a roller 48b (see FIG. 12). The opposite ends of the springs are welded or otherwise secured to the bottom 47 of the box which forms a rigid or nondeformable casing. There is a pressure plate 49 supported on the rollers 48b to be urged upwardly by the prestressed torsion springs, but its upward movement is limited by the flanges 45b.

In each side wall of the box there are vertical, directly opposted slots 51 with an offset notch at the bottom of each, the notch of one slot being reversed with respect to the one for the other slot. The plate 49 has a cross strip 50 across the underside thereof with terminals that extend through the slots. This strip is pivoted at 50a to the center of the plate 49. By pushing down on the ends of this strip the plate 49 can be manually forced down, and then by turning the strip about its pivot through a slight angle, it can be caught in the notches and the plate 49 held down against the pressure of the springs, which function, pantograph-like, to raise the plate 49 when the strip is released. When the plate 49 is moved down and "cocked," the lid may be opened and an empty flask removed and replaced with a full one, as outlined in dotted lines in FIG. 12.

In this modification, the lid is one panel of the casing that provides a pressure panel and plate 49 is the movable pressure panel. The torsion springs function as in FIG. 9, being set away from the movable plate but bearing against its back surface. In this modification the rectangular casing with the flask in place and the lid fastened down, the box may be turned edgewise, or it may be turned completely over so that the springs apply pressure to the flask but do support its weight against gravity.

In this embodiment of our invention, as in others, the spring extension or levers move through an arc of between 30° and 40° in the process of expelling all of the liquid from the bag so that the drop, or the pressure gradient, from fully "cocked" to "flask-empty" position is a relatively small fraction of the total spring pressure and the pressure of outflow of liquid is relatively constant. The box, when in use with the cover closed, comprises a fixed pressure plate confronting the movable, torsion spring-propelled pressure plate inside the casing.

Our invention comprising the garment and the replaceable flask-pressing unit eliminates the movable pole now used to suspend the bag and which must be rolled about with an ambulating or wheelchair patient. It removes from the room floor of the hospital, the cumbersome caster-mobilized pole arrangement and overhead hook fixtures now commonly provided, adding to both the convenience and the well-being of the patient, especially those patients who benefit by walking and perhaps movement from the bedside to a lounge, or merely walking for exercise. It is equally convenient with gravity systems for the nurse and frees more floor space for easy cleaning and minimizes congestion.

In combination with the garment, as previously explained, the apparatus for expelling the liquid from the flask, which we sometimes refer to as the "unit" or "box" or "casing", enables the patient to move about freely and without pulling any support or trailing a lengthy tube about as he moves. Since the catheter or needle is generally entered in the inner arm, the tube which extends from the unit to the shoulder then is normally close against the side of the patient with his arm lowered in a normal walking attitude where it is not likely to become entangled with doorknobs or other protruding objects. The weight of the unit and of the liquid-containing flask is suspended from the shoulders of the wearer and the straps or gussets at the ends of the otherwise open-ended pocket, prevent the unit from sliding from the pocket or pouch while enabling a nurse or other attendant to readily remove the unit for replacement of the flask. With the pocket being open-ended the unit may be reversed end to end for the catheter to be entered at either the right or left side of the patient's body without crossing the patient's body. The pocket desirably is at a level where the unit is below the patient's breast but not so low as to interfere with or be hit by the thighs of the patient when he walks. Perhaps the horizontal axis of the unit is close to the level of the patient's waistline. "Apron strings" on the garment at about waist level keep the pocket with the unit close to the paient's body when he leans over. While the garment and the "box" are used together where the patient is to be mobilized for a period of time, there will be many occasions where it will be more convenient to carry the box in a hand carrier or over-the-shoulder type of bag.

While we have herein particularly referred to the discharge terminal as a needle or a flexible catheter, it may be a terminal which continuously applies liquid at a predetermined rate to an external pad or dressing and the term "needle" includes such a discharge terminal as well as a flexible catheter. Also, while intended particularly for use on humans, it may be used, where needed, with animals.

We claim:

1. In an apparatus for the prolonged intravenous injection of liquid into the body of a patient from a flexible plastic flask having a discharge connection at one end with which one end of a flexible tube is connected, the tube, in turn, having a discharge terminal at its other end, the invention comprising:
 (a) a horizontally elongate four-sided rigid casing of a length, width and depth to recive the flask and having an open end through which the discharge end of the flask is accessible when the container is positioned lengthwise within the casing;
 (b) means in the casing for applying pressure to the flask for collapsing the flask and expelling the liquid therefrom under pressure from the discharge terminal;
 (c) a garment arranged to be worn by the patient having a horizontally extending open-ended pouch removably receiving the casing with the flask therein in a generally horizontal position with its discharge connection selectively accessible at the right or left end of the pouch, the garment being constructed to support the weight of the pouch from the shoulders of the patient when the patient's torso is erect.

2. The apparatus defined in claim 1 wherein the open ends of the pouch have a relatively narrow gusset thereacross at the bottom of the opening to retain the casing against sliding endwise from the pouch but allowing adequate clearance at the ends of the opening to enable the casing to be readily removed and inserted.

3. The apparatus defined in claim 2 wherein said flexible tube is guided from the discharge end of the flask through a retaining loop means at the shoulder area of the garment when the garment is on the patient and the tube is of a length to extend loosely from said shoulder area to the discharge terminal at the point where it is entered in the patient's body and particularly the lower arm above the hand when the hand is in repose below the level of the patient's waist.

4. For use in the administration of liquid by intravenous injection and like sustained applications of liquids to a patient's body at a controlled rate, the apparatus comprising:
 (a) a rigid flat-sided elongate casing of generally rectangular section with two confronting pressure panels extending lengthwise of the casing, at least one of which is movably contained entirely within the casing for movement toward the other to a closed position and away from the other to an open position, the panels providing effectively coextensive opposed surfaces of a length and width to provide between them when in an open position a cavity to receive a liquid filled collapsible plastic bag;
 (b) prestressed torsion spring means within the casing arranged to force the panels transversely of the long axis of the tubular casing when separated toward the closed position and, in so doing, expel the liquid from the plastic bag, the plastic bag having a flexible tube leading from one end thereof to a discharge terminal, and
 (c) means accessible at the exterior of the casing for releasably holding the panels in the open position against the pressure of the torsion springs.

5. The apparatus defined in claim 4 in which one of the rigid flat sides of the casing comprises the said other pressure panel.

6. The apparatus defined in claim 4 in which the movable pressure panel is hinged on hinge means fixed within the casing along one edge of the panel close to and parallel with a corresponding edge of the other panel.

7. The apparatus defined in claim 6 in which the pressure plate hinges about a pintle which is fixed in the casing and the torsion spring means comprises a series of torsion springs along the length of the movable plate with the springs arranged substantially coaxially of the pintle.

8. The apparatus defined in claim 7 in which the casing has top and bottom panels and the bottom panel comprises a resistance plate in cooperating relation with the torsion springs to assure the prestressed condition of the torsion springs through the range of movement of the movable plate.

9. The apparatus defined in claim 8 in which the top panel has a transverse slot extending thereacross and the hinged plate has an operating extension projecting upward through the slot by means of which the hinged plate may be pulled to its open position, the slot having an offset terminal natch into which the lever may be flexed for locking the hinged plate in open position while inserting or removing the flask.

10. The apparatus defined in claim 6 in which the torsion spring means are located on shaft means parallel with but spaced from the pintle shaft and wherein the torsion springs each have a lever-like extension slidably bearing against the distal surface of the movable panel as contrasted to the surface which confronts the opposed pressure panel.

11. The apparatus defined in claim 4 or 6 in which the casing comprises an elongate, generally rectangular rigid tubular body with at least one end of the body being open for insertion of a filled flask into the cavity between said movable panels when the movable one is substantially fully separated to the limit of its movement from the fixed panels, and affording access to the outlet connection at one end of the flask selectively from either end of the casing, depending on the direction from which the flask is inserted.

12. The improvement defined in claim 6 wherein each plate is hinged to move from a vertical plane to a spread open position at a maximum angle of separation which does not exceed 45° whereby the variation in spring pressure from the spread position with the bag horizontally positioned between the plates to the parallel position when the bag is substantially empty remains substantially constant and the progressive expenditure of spring pressure undergoes only unimportant diminution.

13. The apparatus defined in claim 4 in which both pressure panels are hinged to the bottom of the casing between its side walls with torsion spring hinges along their respective bottom edges and wherein the casing has a hinged cover affording access to the space between the panels that open book-like to receive the plastic bag.

14. Apparatus for the intravenous injection of liquid into the body of a patient and similar uses, comprising a metal casing of externally fixed dimension providing:
 (a) a pair of confronting pressure plates having coextensive flat areas, at least one of said plates being hinged for movement from a generally parallel position close against the other to an open position sufficient to enable a collapsible flask to be received between and squeezed when placed between them;

(b) torsion spring means within the casing for urging the plates into a position of parallelism; and (c) means accessible from the exterior of the casing for releasably holding the plates separated against the pressure of the torsion spring means.

15. The apparatus defined in claim 14 in which the casing has top, bottom and side walls, one of which side walls comprises one of the pressure plates which is fixed and only the other plate entirely enclosed within the casing is movable toward and away from said fixed pressure plate, the movable plate having an operating extension at the top thereof and the top of the casing has a transverse slot through which the extension projects, and means at one end of the slot for releasably holding the lever against movement when the plate has been pulled by said lever against the pressure of the torsion spring means when the movable plate has been separated to receive a liquid filled plastic bag between them.

16. In an apparatus for the prolonged intravenous injection of liquid into the body of a patient from a flexible plastic flask having a discharge connection at one end with which a flexible tube is connected, the tube, in turn, having a discharge terminal at its other end, the invention comprising:

(a) a horizontally elongate four-sided rigid casing having an opening at at least one end, the casing being of a length, width and depth to receive the flask containing the liquid to be dispensed therefrom to the body with the casing having an opening through one end through which the discharge terminal of the flask is accessible;

(b) torsion spring actuated means within the casing for applying pressure to the flask therein to forcefully expel the liquid therefrom through the flexible tube to the discharge terminal;

(c) a garment arranged to be positioned about the neck of the patient with a pouch open at each end removably receiving the casing with the flask therein in a generally horizontal position with the end of the flask having the tube connection selectively accessible at the right or left side of the patient with the flask at a level below the shoulders and above the thighs of the patient where it offers minimal impediment to movement of the patient's arms or legs in walking.

17. The apparatus defined in claim 16 wherein the pouch comprises an upwardly folded extension of the fabric of the garment secured by separable fastener means affixed to the garment at a level above the elongate casing when it is positioned in the pouch but below the neck of the patient.

18. The apparatus defined in claim 16 where there is a means on the garment above the level of the pouch for confining the flexible tubing leading from the pouch to a level where it may extend upwardly from the casing and down the patient's upper and lower arm in such manner that the patient may freely move his arm with the tubing extending to shoulder height and then along the patient's arm when the patient extends his arm sideways or forwardly.

* * * * *